United States Patent [19]

Witt

[11] Patent Number: 5,051,358

[45] Date of Patent: Sep. 24, 1991

[54] DIAGNOSTIC METHODS FOR DETECTING PERIODONTAL DISEASES

[75] Inventor: Jonathan J. Witt, Cincinnati, Ohio

[73] Assignee: The Proctor & Gamble Company, Cincinnati, Ohio

[21] Appl. No.: 47,239

[22] Filed: May 7, 1987

[51] Int. Cl.$^5$ .......................... C12Q 1/44; C12Q 1/00
[52] U.S. Cl. .......................................... 435/19; 435/4; 435/805; 435/810
[58] Field of Search .................. 435/19, 805, 810, 30, 435/34

[56] References Cited

U.S. PATENT DOCUMENTS

| | | | |
|---|---|---|---|
| 3,691,018 | 9/1972 | McNamara et al. | 195/103.5 R |
| 3,968,011 | 7/1976 | Manautou et al. | 195/103.5 R |
| 4,296,202 | 10/1981 | Berger et al. | 435/29 |
| 4,299,917 | 11/1981 | Berger et al. | 435/19 |
| 4,499,185 | 2/1985 | Skjold et al. | 435/19 |
| 4,654,298 | 3/1987 | Babb et al. | 435/4 |
| 4,717,652 | 1/1988 | Babb et al. | 435/4 |

FOREIGN PATENT DOCUMENTS

| | | |
|---|---|---|
| 151536 | 8/1985 | European Pat. Off. |
| 158796 | 10/1985 | European Pat. Off. |
| 176246 | 4/1986 | European Pat. Off. |
| 1128371 | 9/1968 | United Kingdom |

OTHER PUBLICATIONS

*Chemical Abstracts*, vol. 69, No. 24, Abstract No. 104511h (1968).

Skougaard et al., "Correlation Between Gingivitis and Orogranulocytic Migratory rate", J. Dent. Res., 48 (suppl. to #5), pp. 716–718 (1969).

Friedman et al., "Experimental Human Gingivitis", J. Periodont, 42(11), pp. 702–705 (1971).

Tenovuo et al., "Application of a Dehydrated Test Strip, HEMASTIX, for the Assessment of Gingivitis", J. Clinical Periodontology, 5, pp. 206–212 (1978).

Anttonon et al., "Experimental Gingivitis in Man Determined by Various Indices with Special Reference to HEMASTIX—Strip Index", pi Proc. Finn. Dent. Soc., 74, pp. 41–45 (1978).

Klinkhamer et al., "Orogranulocyte Peroxidase Activity as a Measure of Inflammatory Periodontal Disease", J. Dent. Res., 58(1), pp. 531–534 (1979).

Friedman et al., "Lysozyme and Lactoferrin Quantitation in the Crevicular Fluid", J. Periodental., 54(6), pp. 347–350 (1983).

Keyes, et al., "A Rationale for Management of Periodontal Diseases: Rapid Identification of Microbial 'Therapeutic Targets' with Phase-Contrast Microscopy" JADA, 106, pp. 803–812 (1983).

Rams et al., "Rationale for the Management of Periodontal Diseases: Effects of Tetracycline on Subgingival Bacteria", JADA, 107, pp. 37–41 (1983).

Herlihy et al., "New and Rapid Method for Detection of Pyuria by Leukocyte Esterase Reaction", Urology, 23(2), pp. 148–149 (1984).

Thurre et al., "Gingival Sulcular Leukocytes in Peridontitis and in Experimental Gingivitis in Humans", J. Periodontal Research, 19, pp. 457–468 (1984).

Singh et al., "In-Vivo Crevicular Leukocyte Response in Humans to a Chemotactic Challenge", J. Peridontol., 55(1), pp. 1–8 (1984).

Smith et al., "Changes in Salivary Peroxidase Activity Observed During Experimentally-Induced Gingivitis", Journal of Clinical Periodontology, 11, pp. 373–378 (1984).

Yamaoka et al., "Relationship Between the Change of Clinical Symptoms and the Value of Salivary Occult Blood Tests on Periodontalily Involved Patients", *Nippon Shishubyo Gakkai Kaishi*, 27(4), pp. 912–923 (1985) (Abstract in English).

Scheer, "The Detection of Leukocyte Esterase Activity in Urine with a New Reagent Strip", Am. J. Clin. Pathol., 87, pp. 86–93 (1987).

Chemstrip LN Package Insert (manufactured by Bio-Dynamics).

*Primary Examiner*—Esther L. Kepplinger
*Assistant Examiner*—Toni Scheiner
*Attorney, Agent, or Firm*—Kim William Zerby; Douglas C. Mohl; Richard C. Witte

[57] ABSTRACT

The present invention relates to diagnostic methods for detecting or evaluating the presence of periodontal diseases, especially gingivitis, in humans or lower animals by measuring the presence of leukocyte esterase. These diagnostic methods comprise measuring the amount of leukocyte esterase present in the oral cavity of the human or lower aniaml being diagnosed.

The present invention further relates to diagnostic products useful in vivo for detecting or evaluating the presence of periodontal diseases, especially gingivitis, in humans. These diagnostic products contain at least one agent useful in detecting the presence of leukocyte esterase, and a carrier material. These diagnostic products must be sterile and safe for in vivo contact with the tissue in the oral cavity of the human being diagnosed.

Finally, the present invention further relates to diagnostic kits useful for detecting or evaluating the presence of periodontal diseases, especially gingivitis, in humans. These kits comprise separate means for collecting a sample of fluid at one or more oral tissue sites in the human being diagnosed, and means for measuring the amount of leukocyte esterase present in the sample collected.

4 Claims, No Drawings

DIAGNOSTIC METHODS FOR DETECTING PERIODONTAL DISEASES

BACKGROUND OF THE INVENTION

The present invention relates to diagnostic methods for detecting or evaluating the presence of periodontal diseases (especially gingivitis) in humans or lower animals by measuring the presence of leukocyte esterase. The present invention further relates to diagnostic products and diagnostic kits useful for detecting or evaluating the presence of periodontal diseases (especially gingivitis) in humans by utilizing agents which detect the presence of leukocyte esterase.

Periodontal diseases, such as, for example, periodontitis, gingivitis, stomatitis, and the like, are inflammatory conditions of the mouth characterized by inflammatory oral tissue changes usually due to local irritation. The destructive inflammatory process involves the interaction between bacteria, food debris, oral leukocytes, and the epithelial attachment around the tooth and periodontal membranes. If allowed to progress unchecked, such inflammatory processes can lead to resorption of the supportive bone around the roots of the teeth and eventual loss of teeth. The early detection of such inflammatory conditions is very important to proper dental treatment.

It has been known for many years that at local sites of inflammation the body produces an increased number of leukocytes. References have suggested measuring the presence of leukocytes for evaluating periodontal health, for example: Rams et al., "A Rationale for Management of Periodontal Diseases: Rapid Identification of Microbial 'Therapeutic Targets' with Phase-Contrasts Microscopy", JADA, 106, pages 803-812 (1983); and Rams et al., "A Rationale for the Management of Periodontal Diseases: Effects of Tetracycline on Subgingival Bacteria", JADA, 107, pages 37-41 (1983); the disclosure of both these articles being incorporated herein by reference in their entirety.

In addition, diagnostic methods for detecting the presence of the inflammatory periodontal disease condition have been developed based on detecting peroxidase enzymes from polymorphonuclear (PMN) leukocytes as described, for example, in "Diagnostic Method for Detecting Periodontal Disease", European Patent Application Publication No. 158796, by Richardson-Vicks Inc., published Oct. 23, 1985, the disclosure of which is incorporated herein by reference in its entirety. Reagents for assessing periodontal diseases by detecting the presence of peroxidases and/or salivary occult blood in the oral cavity are known, having been described in: Tenovuo and Anttonen, "Application of a Dehydrated Test Strip, HEMASTIX®, for the Assessment of Gingivitis", J. of Clinical Periodontology, 5, pages 206-212 (1978); Anttonen et al., "Experimental Gingivitis in Man Determined by Various Indices with Special Reference to HEMASTIX®-Strip Index", Proc. Finn. Dent. Soc., 74, pages 41-45 (1978); Ueda et al., "Assessment of Gingival Bleeding with a Salivary Occult Bleeding Test Strip", Bull. Josai Dent. Univ., 13 (3), pages 628-633 (1984); Yamaoka et al., "Relation between Changes in the Clinical Symptoms in the Value of Salivary Occult Blood Tests in Periodontally Involved Patients—A Study Using a Test Paper for Saliva Examination (Salivaster Bld)", Nippon Shishubyo Gakkai Kaishi, 27, (4), pages 912-922 (1985); and Smith et al., "Changes in Salivary Peroxidase Activity Observed During Experimentally-Induced Gingivitis", J. Clin. Periodontol. (Denmark), 11, (6), pages 373-378 (1984); the disclosures of all these publications being incorporated herein by reference in their entirety.

Thus, while there has been much research into methods for detecting periodontal diseases, none of these references disclose or discuss measuring leukocyte esterase as a method for detecting periodontal diseases. In fact, one publication relating to the use of reagent strips to indicate the presence of leukocyte esterase in urine for detecting whether a patient has pyuria (Kusumi et al., JAMA, 245 (16), pages 1653-1655 (1981); the disclosure of which is incorporated herein by reference in its entirety) specifically speculates that the leukocyte esterase test "cannot, however, be used to test sputum, since saliva is rich in esterase activity." Therefore, the present invention is clearly surprising in light of the published literature.

An object of the present invention is to provide methods for detecting the presence of periodontal diseases (especially gingivitis) in humans or lower animals. Another object is to provide methods for evaluating the severity of periodontal diseases (especially gingivitis) in humans or lower animals. An object of the present invention is also to provide methods for following diseased gingival sites for improvement during the course of therapy; and for targeting gingival sites that are susceptible to gingivitis, prior to overt inflammation, for further monitoring or preventative treatment. A further object is to provide diagnostic products useful in vivo for detecting or evaluating the presence of periodontal diseases in humans. A still further object is to provide diagnostic kits useful for detecting or evaluating the presence of periodontal diseases in humans.

These and other objects of the present invention will become readily apparent from the detailed description which follows.

All percentages and ratios used herein are by weight unless otherwise specified.

SUMMARY OF THE INVENTION

The present invention relates to diagnostic methods for detecting or evaluating the presence of periodontal diseases, especially gingivitis, in humans or lower animals. These methods comprise measuring the amount of leukocyte esterase present in the oral cavity of the human or lower animal being diagnosed.

The present invention further relates to diagnostic products useful in vivo for detecting or evaluating the presence of periodontal diseases, especially gingivitis, in humans. These diagnostic products contain at least one agent useful in detecting the presence of leukocyte esterase, and a carrier material. These diagnostic products must be sterile and safe for in vivo contact with the tissue in the oral cavity of the human being diagnosed.

Finally, the present invention relates to diagnostic kits useful for detecting or evaluating the presence of periodontal diseases, especially gingivitis, in humans. These kits comprise separate means for collecting a sample of fluid at one or more oral tissue sites in the human being diagnosed, and means for measuring the amount of leukocyte esterase present in the sample collected.

DETAILED DESCRIPTION OF THE INVENTION

Methods for Diagnosing Periodontal Diseases

The present invention relates to diagnostic methods for detecting or evaluating the presence of periodontal diseases (especially gingivitis) in humans or lower animals. These methods comprise measuring the amount of leukocyte esterase present in the oral cavity of the human or lower animal being diagnosed.

"Detecting or evaluating the presence of periodontal diseases", as used herein, means detecting the presence of, or evaluating the severity of, periodontal diseases. The term "periodontal diseases", as used herein, means inflammatory conditions of the mouth, whether or not discernible to the naked eye, including such inflammatory conditions as periodontitis, stomatitis, and gingivitis. The method of the present invention is particularly useful for detecting the presence of gingivitis which is not readily discernible to the naked eye, and for evaluating the severity of gingivitis whether or not discernible to the naked eye. Thus, the methods of the present invention are especially suited for predicting the onset of gingivitis and/or for quantitatively or semi-quantitatively indicating the degree of the severity of gingivitis. As a result of this early detection, early dental treatment can be initiated to ensure rapid return to proper dental health.

"Measuring the amount of leukocyte esterase present in the oral cavity", as used herein, means either simply detecting the presence of leukocyte esterase; or quantitatively or semi-quantitatively measuring the concentration of leukocyte esterase in the oral cavity. These measurements can be made either at one or more particular oral sites (preferably at gingival sites, and most preferably at the gingival margin), or in the saliva generally. Products and/or reagents which may be utilized for measuring the amount of leukocyte esterase present in the oral cavity are described more fully hereinafter.

The methods of the present invention may be carried out in many ways, including, but not limited to: (1) in vivo or in vitro measurement of a saliva sample; (2) in vitro measurement of a sample from a specific gingival site or sites; and (3) in vivo measurement of the leukocyte esterase activity at a specific gingival site or sites. Each of these procedures is further elaborated immediately hereinafter to illuminate and exemplify the methods of the present invention.

In vitro measurement of the leukocyte esterase activity in saliva samples is preferably accomplished by utilizing commercially-available leukocyte esterase reagent strips suitable for in vitro evaluation of leukocyte esterase activity. The saliva sample may be expectorated directly onto the strip, or, preferably, is diluted in water to a certain volume and tested by dipping the reagent strip in the dilute saliva sample. It is further preferred that the subject to be diagnosed not eat within one hour prior to the sample collection.

Examples of commercially-available leukocyte esterase reagent strips are CHEMSTRIP® 9 and CHEMSTRIP® LN (both sold by Bio-Dynamics, Indianapolis, Ind.); and MULTISTIX® 2 Reagent Strips and AMES LEUKOSTIX® (both available from Ames, Division of Miles Laboratory, Elkhart, Ind.). Techniques for using these commercially-available leukocyte esterase reagent strips are well known from their use for in vitro urine analysis (e.g., Scheer, "The Detection of Leukocyte Esterase Activity in Urine with a New Reagent Strip", *Am. J. Clin. Pathol.*, 87 (1), pages 86-93 (1987), the disclosures of which are incorporated herein by reference in their entirety). These known urine analysis techniques are applicable to the in vitro methods of the present invention.

All of these commercially-available leukocyte esterase reagent strips contain an indoxyl carbonic acid ester which is hydrolyzed to indoxyl by leukocyte esterase. The indoxyl thus formed reacts with a diazonium compound in the strip to produce a color which indicates the presence of the leukocyte esterase. The degree of darkening of the strips is a semi-quantitative indication of the amount of leukocyte esterase present in the saliva sample, and hence for the methods of the present invention is an indication of the severity of the periodontal disease. The presence of color change when no periodontal diseases are readily evident to the naked eye may indicate the onset of gingivitis.

In vitro measurement of a sample obtained from a specific gingival site is a preferred method of the present invention. The sample collection may be accomplished in many ways, but preferred is flushing a region with fluid and then micropipetting a sample of fluid directly from the site of the gingival surface, or more preferably swabbing the gingival site. It is also preferred for these in vitro measurements that the subject to be diagnosed rinse his mouth or brush his teeth within one hour prior to sample collection. The sample collected may be applied directly to a commercially-available leukocyte esterase reagent strip such as described hereinbefore (e.g., CHEMSTRIP® LN; MULTISTIX® Reagent Strips), but preferably the sample is diluted to a certain volume and then the dilute sample is tested by dipping the reagent strip into the solution or by applying some of the solution to the reagent strip. The preferred commercially-available leukocyte esterase reagent strip for this procedure is CHEMSTRIP® LN which contains 5.8 micrograms of indoxyl carbonic acid ester (as described in the "CHEMSTRIP® LN" package insert, the disclosures of which are incorporated herein by reference in their entirety). Also useful for this in vitro procedure are the diagnostic kits of the present invention described more fully hereinafter.

In vivo measurements of leukocyte esterase present in the oral cavity may be accomplished by testing the saliva in the mouth or by measuring the leukocyte esterase activity at specific gingival sites. These in vivo measurements are preferably accomplished by utilizing a diagnostic product of the present invention or a suitable diagnostic kit of the present invention, both described more fully hereinafter. The in vivo measurement of saliva typically involves placing the diagnostic product of the present invention, or the appropriate component of the diagnostic kit of the present invention, into the mouth so that it is bathed with saliva. The in vivo measurement of specific gingival sites preferably involves contacting the diagnostic product of the present invention, or the appropriate component of the diagnostic kit of the present invention, with the gingival site being evaluated. Typical in vivo contact time is about 0.1 to about 60 seconds followed by removal of the diagnostic product or kit component for observation (e.g., for a color change) or further manipulation (e.g., in the case of a kit, preferably to develop a color change).

For purposes of the methods of the present invention, it is preferred that the measurement of the amount of leukocyte esterase present in the oral cavity be indicated by reagents which indicate leukocyte esterase activity through color change. Such reagents are described more fully in the following publications, the disclosures of which are incorporated by reference herein in their entirety: Herlihy et al., "New and Rapid Method for Detection of Pyuria by Leukocyte Esterase Reaction", *Urology*, 23 (2), pages 148-149 (1984); U.S. Pat. No. 4,499,185, to Skjold et al., issued Feb. 12, 1985; U.S. Pat. No. 4,331,760, to Berger et al., issued May 25, 1982; U.S. Pat. No. 4,296,202, to Berger et al., issued Oct. 20, 1981; European Patent Application Publication No. 158,204, Miles Laboratories Inc., published Oct. 16, 1985; European Patent Application Publication No. 157,326, Miles Laboratories Inc., published Oct. 9, 1985; European Patent Application Publication No. 157,327, Miles Laboratories Inc., published Oct. 9, 1985; European Patent Application Publication No. 157,360, Miles Laboratories Inc., published Oct. 9, 1985; European Patent Application Publication No. 157,361, Miles Laboratories Inc., published Oct. 9, 1985; and European Patent Application Publication No. 157,362, Miles Laboratories Inc., published Oct. 9, 1985. The sensitivity of such colorimetric indicators is preferably such that no color change is indicated for levels of leukocyte esterase activity typically observed in humans in good dental health but color change is indicated for levels slightly elevated above the normal healthy levels.

Diagnostic Products

The present invention also relates to diagnostic products useful in vivo for detecting or evaluating the presence of periodontal diseases in humans. These diagnostic products comprise at least one agent useful in detecting the presence of leukocyte esterase, and a carrier material. Furthermore, since these diagnostic products are to be utilized in vivo in humans, these diagnostic products must be sterile and safe for in vivo contact with the tissue of the oral cavity, especially gingival tissue, of a human.

The term "agent useful in detecting the presence of leukocyte esterase", as used herein, means an organic or inorganic compound, composition, or combination thereof which is changed by the action of leukocyte esterase or is bound by leukocyte esterase or is otherwise modified in the presence of leukocyte esterase such that the presence of leukocyte esterase can be detected, preferably quantitatively or semi-quantitatively, as a result of this change, binding, or other modification.

Preferred agents useful for detecting the presence of leukocyte esterase are esters hydrolyzable by leukocyte esterase. More preferred are esters which are hydrolyzable by leukocyte esterase to produce a color or change color. This color or color change may be the result of either: (a) one or more of the ester hydrolysis products themselves; or (b) one or more of the ester hydrolysis products combining with one or more other materials (which may or may not be present in the diagnostic product) to produce a color or color change. Most preferred are indoxyl carbonic acid esters which are hydrolyzed by leukocyte esterase to form indoxyl. Such esters are utilized in the commercially available leukocyte esterase reagent strips as disclosed, for example, in Herlihy et al., "New and Rapid Method for Detection of Pyuria by Leukocyte Esterase Reaction", *Urology*, 23 (2), pages 148-149 (1984); and Scheer, "The Detection of Leukocyte Esterase Activity in Urine with a New Reagent Strip", *Am. J. Clin. Pathol.*, 87 (1), pages 86-93 (1987), disclosures of both these publications being incorporated by reference herein in their entirety. The amount of ester hydrolyzable by leukocyte esterase present in the diagnostic products of the present invention is preferably from about 1 microgram to 1 g, more preferably from about 1 microgram to 0.01 g, and most preferably from about 1 microgram to 100 micrograms.

If the ester hydrolyzed by leukocyte esterase produces a color or changes color when hydrolyzed by leukocyte esterase, then typically no chromogenic material need be included in the diagnostic product. However, when the products of the ester hydrolysis do not produce a color or change color, or produce or change colors less dramatically than desired, then a chromogenic material is preferably added to the diagnostic carrier. The term "chromogenic material", as used herein, means an organic or inorganic compound, composition, or combination thereof which produce a color or change color in the presence of the products resulting from the hydrolysis of the ester hydrolyzable by leukocyte esterase. It is to be noted that while this is preferred, the diagnostic products of the present invention include diagnostic products containing esters hydrolyzable by leukocyte esterase which esters do not produce a color or change color, and which products do not contain a chromogenic material. Such diagnostic products are preferably treated, after use in the oral cavity, with a chromogenic material (e.g., a solution containing a chromogenic material) to thereby produce a color or change color indicating whether ester hydrolysis by leukocyte esterase has occurred.

By the diagnostic products of the present invention being "safe for in vivo contact with the tissue of the oral cavity of a human", as used herein, is meant that the agents useful in detecting the presence of leukocyte esterase and the carrier materials are safe to be in contact with the tissue in the oral cavity of a human, or if not safe to be in contact with the tissue in the oral cavity of a human then they are safely isolated within the diagnostic product so that they cannot contact the tissue in the oral cavity of a human, as determined by sound medical judgment (at a reasonable risk/benefit ratio). Most preferred is that all the agents useful in detecting the presence of leukocyte esterase and all the carrier materials themselves are safe.

Agents useful in detecting the presence of leukocyte esterase are known, having been disclosed for example in the following publications whose disclosures are incorporated by reference herein in their entirety: Herlihy et al., "New and Rapid Method for Detection of Pyuria by Leukocyte Esterase Reaction", *Urology*, 23 (2), pages 148-149 (1984); U.S. Pat. No. 4,499,185, to Skjold et al., issued Feb. 12, 1985; U.S. Pat. No. 4,331,760, to Berger et al., issued May 25, 1982; U.S. Pat. No. 4,296,202, to Berger et al., issued Oct. 20, 1981; European Patent Application Publication No. 158,204, Miles Laboratories Inc., published Oct. 16, 1985; European Patent Application Publication No. 157,326, Miles Laboratories Inc., published Oct. 9, 1985; European Patent Application Publication No. 157,327, Miles Laboratories Inc., published Oct. 9, 1985; European Patent Application Publication No. 157,360, Miles Laboratories Inc., published Oct. 9, 1985; European Patent Application Publication No. 157,361, Miles Laboratories Inc., published Oct. 9, 1985; and European Patent Application Publication No. 157,362, Miles Laboratories Inc., published Oct. 9, 1985. While certain of the compositions and products described in these publications may be useful as diagnostic products of the present invention if modified according to the present invention, these publications do not describe diagnostic products which are processed and prepared to be sterile and safe for in vivo diagnostic use in the oral cavity of humans according to the present invention.

The term "carrier material", as used herein, means one or more materials which are compatible with the agent useful in detecting the presence of leukocyte esterase and with the leukocyte esterase itself. The term "compatible", as used herein, means that the carrier materials are suitable for use in diagnostic products such that the ability of the agent to detect leukocyte esterase is not adversely affected during normal use of the diagnostic product. Various materials from which the carrier materials for the present diagnostic products may be selected are provided in several of the publications incorporated by reference hereinbefore, as well as in the following patents which are incorporated herein by reference in their entirety: U.S. Pat. No. 4,587,099, to Rothe et al., issued May 6, 1986; U.S. Pat. No. 4,604,264, to Rothe et al., issued Aug. 5, 1986; U.S. Pat. No. 4,592,893, to Poppe et al., issued June 3, 1986; and U.S. Pat. No. 4,605,629, to Lange et al., issued Aug. 12, 1986.

The diagnostic products of the present invention are designed such that they are suitable for use in the oral cavity of humans. Thus, these products are appropriately sized and structured to fit into the oral cavity of a human and to contact the tissue of the oral cavity to be diagnosed. Preferred are diagnostic products in the form of a strip which has the agent useful in detecting the presence of leukocyte esterase positioned at one end of the strip. These diagnostic strips are used by contacting the agent-containing end of the strip with the tissue to be diagnosed for a few seconds (typically about 0.1 to about 60 seconds). Another form of the diagnostic products useful for whole mouth diagnosis is a moldable mouthpiece. This product contains the agent useful in detecting the presence of leukocyte esterase distributed throughout the mouthpiece. The mouthpiece is used by biting down on the mouthpiece for a few seconds. These are just two examples of a wide variety of forms suitable for use in the oral cavity for the diagnostic products of the present invention.

The agent useful in detecting the presence of leukocyte esterase typically comprises from about 0.00001% to about 10% of the diagnostic product of the present invention, and preferably from about 0.001% to about 1%. The carrier material typically comprises from about 90% to about 99.99999% by weight of the diagnostic product of the present invention, and preferably from about 99% to about 99.999%.

Diagnostic Kits

The present invention further relates to diagnostic kits useful for detecting or evaluating the presence of periodontal diseases in humans. These kits comprise separate means for collecting a sample of fluid at one or more oral tissue sites (especially gingival sites) in a human being diagnosed, and means for measuring the amount of leukocyte esterase present in the sample collected.

The phrase "means for collecting a sample of fluid", as used herein, means any device or apparatus or product which is useful for removing a sample of fluid (which may also include solid tissue matter) from the oral cavity for further analysis without adversely affecting the ability to detect the presence of leukocyte esterase activity in the sample of fluid collected. Non-limiting examples of such means are swabs, pipettes, syringes, absorbent tapes, absorbent gauzes, absorbent strips, scoops, suction bulbs, and aspirators. Preferred means are swabs and absorbent strips. Absorbent strips useful in the kits of the present invention may also be diagnostic products of the present invention which contain the agent useful in detecting the presence of leukocyte esterase, but which must be mixed with a chromogenic material after removal from the mouth to indicate the presence of leukocyte esterase activity. Thus, a kit of the present invention may comprise one or more diagnostic products of the present invention.

The phrase "means for measuring the amount of leukocyte esterase", as used herein, means a machine or product or device or combination thereof which is capable of showing the presence of leukocyte esterase in a sample of fluid collected as described hereinbefore. Preferably, such means are capable of quantitatively, or more preferably semi-quantitatively (especially by color change), indicating the amount of leukocyte esterase present in the sample collected. Non-limiting examples of such means are leukocyte esterase reagent strips comprising indoxyl carbonic acid esters; and solutions containing chromogenic material. Preferred are the commercially available leukocyte esterase reagent strips comprising an indoxyl carbonic acid ester such as the AMES LEUKOSTIX, CHEMSTRIP 9, and especially the CHEMSTRIP LN.

The kits of the present invention are manufactured such that the means for collecting a sample of fluid and the means for measuring the amount of leukocyte esterase are separate components in the kits, and these essential components plus any optional components to be utilized with the kits (e.g., test tubes for diluting samples in; bottles containing dilution fluid for diluting samples; instruction sheets; etc.) are combined into one package. An example of such a package is a box which is shrink wrapped with plastic.

The following examples further describe and demonstrate embodiments within the scope of the present invention. The examples are given solely for the purpose of illustration and are not to be construed as limitations of the present invention as many variations thereof are possible without departing from the spirit and scope.

EXAMPLE I

In Vitro Saliva Sample Assay

Ten ml of a 0.9% saline solution is dispensed into a sterile container. Using this saline solution the patient (who has been instructed not to eat within the last hour) rinses his mouth for 30 seconds, after which time the rinse is returned to the container. This rinse is tested with the CHEMSTRIP 9 leukocyte esterase diagnostic strip (sold by Bio-Dynamics, Indianapolis, Ind.) by briefly (no longer than 1 second) dipping the test strip into the saline rinse. The chemically impregnated patches on the test strip are totally immersed in the saline rinse before removal. Upon removal of the test strip from the solution, the edge of the test strip is drawn along the rim of the specimen container to remove excess rinse solution. Approximately 60 to 120 seconds after dipping the strip in the rinse solution, the test strip is read for leukocyte esterase activity by holding the strip in the same direction as when it was dipped into the saline and then carefully matching the patches with the proper color blocks provided on the color chart provided with the CHEMSTRIP 9 product. Color changes that occur after 2 minutes from immersion are not of diagnostic value. Color changes that occur only along the edge of the test area are ignored (careful removal of excess saline should eliminate this effect).

This diagnostic method correlates very well with the clinically observed gingival inflammation (GI) index. The GI index measurement is fully described in Loe, "The Gingival Index, the Plaque Index and the Retention Index Systems", *J. Periodontology*, 38, pp. 610–616 (1967); and Silness and Loe, "Periodontal Disease in Pregnancy. I. Prevalence and Severity", *Acta Odont. Scand.*, 21, pp. 533–551 (1963), the disclosures of both these articles being incorporated by reference herein in their entirety.

EXAMPLE II

In Vitro Gingival Site Assay

In order to determine the relationship of gingivitis at specific gingival site to the presence of leukocytes at those sites, and to relate changes in gingival scores over time, the following diagnosis protocol is followed.

Gingival inflammation is scored using the standard GI index with each tooth site classified as 0, 1, 2, or 3. After the patient's gingival sites are scored, the results are evaluated and three test teeth are selected per individual. Three teeth, with scores of 0, 1, and 2, are chosen in the upper maxilla for sampling. If all three scores are not available in the upper jaw, then mandibular teeth are selected. The tooth and gum at each site are briefly air-dried to remove saliva. A Type 4 Calgiswab ® (sold by Spectrum Laboratories, Inc., Houston, Tx.) swab is gently rolled in the crevicular margin for approximately 10 seconds. The swab is then immediately transferred to a plastic tube containing 1 ml of normal aqueous saline solution. The swab is gently swirled in the saline and the tube briefly agitated to disperse the collected material. After a minimum time of 30 seconds (preferably 10 to 20 minutes), a 20 microliter aliquot of the sample solution is pipetted onto a CHEMSTRIP LN leukocyte esterase diagnostic strip (sold by Bio-Dynamics, Indianapolis, Ind.). The color change is then recorded at 1 and 2 minutes after the solution is added to the diagnostic strip.

Following this procedure it is determined that there is very good correlation between the clinically observed GI index and the CHEMSTRIP LN evaluation. It is also determined that the CHEMSTRIP LN diagnostic strip is predictive of the onset of gingivitis, and predictive of healthy improvement in diseased gingival sites during the course of therapy.

EXAMPLE III

In Vivo Diagnostic Product

An in vivo diagnostic product of the present invention is prepared as follows. This diagnostic product is a modified version of a test strip disclosed in U.S. Pat. No. 4,499,185, to Skjold et al., issued Feb. 12, 1985, the disclosures of which are incorporated herein by reference in their entirety. That test strip has been modified according to the present invention such that all materials and solutions used to prepare this diagnostic product are sterile and sufficiently pure to manufacture a diagnostic product which is sterile and safe for contact in vivo with gingival tissue of humans.

A piece of Eaton and Dikeman 205 filter paper is briefly immersed in a first dip solution and dried in an air oven at 100° C. for 20 minutes. This first dip solution comprises a borate buffer solution to which is added an anionic detergent (Bio-Terge AS-40; available from Stepan Chemical Co.) and potassium bromate. The borate buffer (pH=8.6) is prepared by adding 4.5 ml of a 0.2M boric acid solution to 5.5 ml of 0.05M borax solution, all in distilled water. To this solution is added a sufficient volume of Bio-Terge AS-40 to produce a 0.2 ml/dl solution. The resulting solution is then made 10 mM in potassium bromate.

The dried filter paper following the first dip is then immersed in a second dip solution and dried in an air oven at 60° C. for 5 minutes. This second dip solution comprises an acetone solution of polyvinylpyrrolidone, n-decanol, quinine hydrochloride, and 3-(N-tosyl-L-alanyl-oxy)indole. The resulting concentrations of the solutes are: 1 ml/dl polyvinylpyrrolidone and in methanol (Luviskol available from GAF Corporation); 2 ml/dl n-decanol; 10 mM quinine hydrochloride; and 2 mM 3-(N-tosyl-L-alanyl-oxy)indole.

A square (2 mm on a side) of the dried filter paper is then mounted at one end of a polystyrene strip (measuring about 10 cm×0.2 cm). Adhesion between the filter paper and the polystyrene strip is achieved through the use of a double-faced adhesive tape (Double Stick; available from the 3M Company). The resulting sterile and safe diagnostic strip is then individually packed in a sterile plastic wrap.

This diagnostic strip of the present invention is used to diagnose periodontal diseases as follows. The tooth and gum at a gingival site are briefly air-dried to remove saliva. The filter paper on the end of the diagnostic product is then placed against this gingival site for approximately 5 seconds, after which time the strip is removed from the site and the mouth. After about 15 minutes sufficient color has developed in the strip to enable a determination of a positive test. More rapid development of a color change (in about 1 to 2 minutes) may be accomplished by spraying (immediately following removal of the strip from the mouth) the filter paper on the diagnostic strip with an ethanol solution containing a diazonium salt.

EXAMPLE IV

Diagnostic Kit Useful for In Vitro Gingival Site Assay

A diagnostic kit useful for the in vitro gingival site assay as described hereinbefore in Example II contains the following components: one Type 4 Calgiswab ® swab (sold by Spectrum Laboratories, Inc., Houston, Tex.); one CHEMSTRIP LN leukocyte esterase diagnostic strip (sold by Bio-Dynamics, Indianapolis, Ind.); one plastic tube marked to indicate 1.0 ml volume. These components, along with an instruction sheet describing the in vitro method outlined hereinbefore in Example II, are packaged in a box wrapped with plastic.

This kit is utilized as described in the in vitro method of Example II, with the user utilizing tap water in place of the saline solution and dipping the CHEMSTRIP LN into the sample solution. This kit provides a quick and easy method for the user to semi-quantitatively diagnose the gingival health of specific gingival sites, to identify gingival sites which may be deteriorating toward gingivitis, and to indicate healthy improvement in diseased gingival sites during therapy.

What is claimed is:

1. A method for determining the presence of or evaluating periodontal disease in humans or lower animals, comprising:

contacting saliva from the human or lower animal being diagnosed with a leukocyte esterase detection reagent, determining the amount of leukocyte esterase present in the saliva, and correlating the amount of leukocyte esterase present in the saliva with a standard indicative of the presence or absence of periodontal disease.

2. A method for determining the presence of or evaluating periodontal disease in humans or lower animals, comprising:

contacting saliva from the human or lower animal being diagnosed with a leukocyte esterase detection reagent, determining the amount of leukocyte esterase present in the saliva colorimetrically, wherein no color change is an indication of good dental health and a color change is an indication of periodontal disease.

3. The method of claim 2 wherein the leukocyte esterase detection reagent includes an ester hydrolyzable by leukocyte esterase.

4. The method of claim 3 wherein the ester hydrolyzable by leukocyte esterase is an indoxyl carbonic acid ester which is hydrolyzable to form indoxyl and wherein formation of indoxyl produces a color change.

* * * * *